United States Patent
LaVoie et al.

[11] Patent Number: 5,770,617
[45] Date of Patent: Jun. 23, 1998

[54] TERBENZIMIDAZOLES USEFUL AS ANTIFUNGAL AGENTS

[75] Inventors: Edmond J. LaVoie, Princeton Junction; Leroy Fong Liu, Bridgewater, both of N.J.; Qun Sun, Zhejiang, China

[73] Assignee: Rutgers, The State University of New Jersey, New Brunswick, N.J.

[21] Appl. No.: 786,629

[22] Filed: Jan. 21, 1997

Related U.S. Application Data

[63] Continuation-in-part of Ser. No. 618,988, Mar. 20, 1996.

[51] Int. Cl.$^6$ .................................................. A61K 31/415
[52] U.S. Cl. ........................................ 514/394; 548/305.4
[58] Field of Search ............................................... 514/394

[56] References Cited

U.S. PATENT DOCUMENTS

| | | | |
|---|---|---|---|
| 5,639,755 | 6/1997 | Dykstra et al. | 514/394 |
| 5,643,935 | 7/1997 | Dykstra et al. | 514/394 |

*Primary Examiner*—Mukund J. Shah
*Assistant Examiner*—Pavanaram K. Sripada
*Attorney, Agent, or Firm*—Schwegman, Lundberg, Woessner & Kluth, P.A.

[57] ABSTRACT

The present invention provides a method of treatment of fungal infection with an antifungal topoisomerase I inhibitor of the formula:

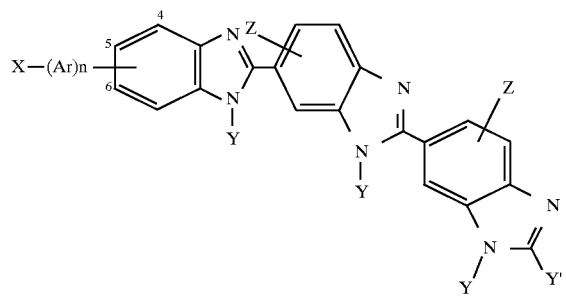

wherein Ar is $(C_6-C_{12})$aryl, a (5- to 12-membered) heteroaryl comprising 1–3 N, S or non-peroxide O, wherein N is unsubstituted or is substituted with H, $(C_1-C_4)$alkyl or benzyl; or benzo; X is H, CN, CHO, OH, acetyl, $CF_3$, $O(C_1-C_4)$alkyl, $NO_2$, $NH_2$, halogen or halo-$(C_1-C_4)$alkyl; each Y is individually H, $(C_1-C_4)$alkyl or aralkyl; Y' is H or $(C_1-C_4)$alkyl; n is 0 or 1; and each Z is individually H, $(C_1-C_4)$alkyl, halogen or halo$(C_1-C_4)$alkyl; or a pharmaceutically acceptable salt thereof.

24 Claims, 9 Drawing Sheets a) X=H, Y=Cl
b) X=Br, Y=H
c) JSK IV-44 a) JSK IV-67, i), X=Cl
b) JSK IV-35, i), X=Br
c) JSK IV-46, ii), X=p-CHLOROPHENYL a) JSK IV-68, X=Cl
b) JSK IV-37, X=Br
c) JSK IV-47, X=p-CHLOROPHENYL

| FIG. 8A |
|---|
| FIG. 8B |

FIG. 8B

TERBENZIMIDAZOLES USEFUL AS ANTIFUNGAL AGENTS

CROSS-REFERENCE TO RELATED APPLICATIONS

This application is a continuation-in-part of Ser. No. 08/618,988, filed Mar. 20, 1996, pending.

This invention was made with the support of NIH Grant CA 39962. The Government has certain rights in the invention.

BACKGROUND OF THE INVENTION

DNA topoisomerases are nuclear enzymes that control and modify the topological states of DNA by catalyzing the concerted breaking and rejoining of DNA strands. See, for example, D'Arpa et al., Biochim. Biophys. Acta, 989, 163 (1989). Topoisomerase II enzymes alter the topological state of DNA by means of a double strand break in the DNA. By interfering with the breakage/reunion reaction of DNA topoisomerases, a number of agents have been shown to convert these enzymes into net DNA-breaking enzymes, resulting in efficient cell killing. See L. F. Liu, in Topoisomerases: topoisomerase targeting drugs, Adv. in Pharmacol., 29B (1994); L. K. Wang et al., Chem. Res. Toxicol., 6, 813 (1993). Thus, mammalian topoisomerase II represents an effective pharmacological target for the development of cancer chemotherapeutics. (A. Y. Chen et al., Annu. Rev. Pharmacol. Toxicol., 34, 191 (1994)). Among the clinical agents in use which are recognized as topoisomerase II inhibitors are etoposide (VP-16), teniposide (VM-26), mitoxantrone, m-AMSA, adriamycin (doxorubicin), ellipticine and daunomycin.

In comparison to topoisomerase II inhibitors, there are relatively few known topoisomerase I inhibitors. Camptothecin represents the most extensively studied mammalian topoisomerase I inhibitor. See R. C. Gallo et al., J. Natl. Cancer Inst., 46, 789 (1971) and B. C. Giovanella et al., Cancer Res., 51, 3052 (1991). The interference of camptothecin with the breakage/reunion reaction of topoisomerase I, results in accumulation of a covalent intermediate, in which topoisomerase I is reversibly trapped in a cleaved state, termed the cleavable complex (Y.-H. Hsiang et al., J. Biol. Chem., 260, 14873 (1985); S. E. Porter et al., Nucl. Acids Res., 17, 8521 (1989); C. Jaxel et al., J. Biol. Chem., 266, 20418 (1991)). The broad spectrum of potent antineoplastic activity observed for camptothecin has prompted further efforts to identify other agents which can effectively poison mammalian topoisomerase I.

It has recently been demonstrated that Hoechst 33342 (1), 2'-(4-ethoxyphenyl)-5-(4-methyl-1-piperazinyl)-2,5'-bi-1H-benzimidazole, is an inhibitor of topoisomerase I.

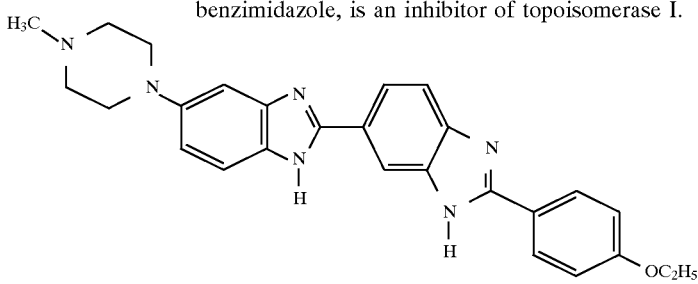

1

This agent, which binds to the minor groove of DNA, traps the reversible cleavable complex derived from DNA and topoisomerase I and produces a limited number of highly specific single-strand DNA breaks. For example, see A. Y. Chen et al., Cancer Res., 53, 1332 (1993) and A. Chen et al., PNAS, 90, 8131 (1993). A limitation of Hoechst 33342 as an anticancer agent is the previously reported observation that it is not effective against tumor cell lines which overexpress MDR1. While KB 3-1 cells are known to be quite sensitive to Hoechst 33342, with an $IC_{50}$ of approximately 9 nM, this compound is approximately 130-fold less cytotoxic to KB V-1 cells, which are known to overexpress MDR1. Recently, several analogs of this bisbenzimidazole have been synthesized, to further investigate the structure activity relationships associated with their potency as mammalian topoisomerase I inhibitors and the related cytotoxicity. For example, Q. Sun et al., Biorg. and Med. Chem, Lett., 4, 2871 (1994) disclosed the preparation of bis-benzimidazoles of formula (2):

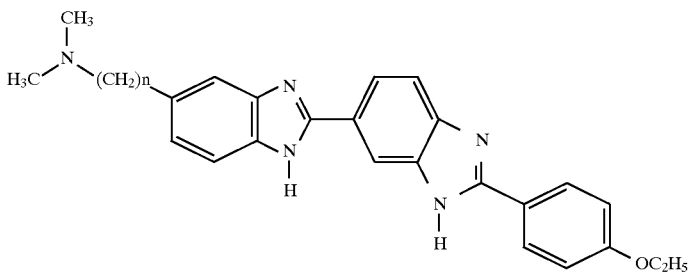

2 where n is 0, 1, 2, or 3. However, these compounds were found to be about one order of magnitude less cytotoxic than Hoechst 33342.

More recently, Q. Sun et al., in Abstract 2688, Scientific Proceedings-86th Annual Meeting of the AACR (Toronto, CA, Mar. 18–22, 1995) disclosed that a trisbenzimidazole derivative, 5-(2-pyridyl)-2- [2'-benzimidazol-5"-yl benzimidazol-5'-yl]benzimidazole has similar potency as an inhibitor of human topoisomerase I as Hoechst 33342.

Mycotic infections have become increasingly important in the last two decades, causing high mortality among immunocompromised patients, such as transplant recipients and cancer and AIDS patients. The expanding patient population and some existing problems in current antifungal chemotherapy have created a demand for more effective and safe antifungal agents for the treatment of this increasingly important class of opportunistic infections. Based on studies in *Saccharomyces cerevisiae* and *Candida albicans*, nuclear fungal topoisomerase I shows promise as a molecular target for antifungal agents (see J. M. Fostel et al., *Antimicrob. Agents Chemother.*, 39, 586 (1995); J. M. Fostel et al., *Antimicrob. Agents Chemother.*, 39, 2131 (1992)). Studies in *S. cerevisiae* have established topoisomerase I to be a fungicidal target for camptothecin (J. Nitiss et al., *PNAS USA*, 85, 7501 (1988)). Studies in *C. albicans* have demonstrated differences in sensitivity of the human and Candida topoisomerase I to the aminocatechol A-3253 (J. M. Fostel (1995) cited above).

*Aspergillus fumigatus* and *A. niger* are two important life-threatening systemic human pathogens. There is an urgent need for more effective antifungal agents for the treatment of patients with these opportunistic infections.

SUMMARY OF THE INVENTION

The present invention provides a therapeutic method for the treatment of a fungal infection comprising administering to a mammal afflicted with a fungal infection, particularly a systemic fungal infection, an effective antifungal amount of a compound of general formula (I):

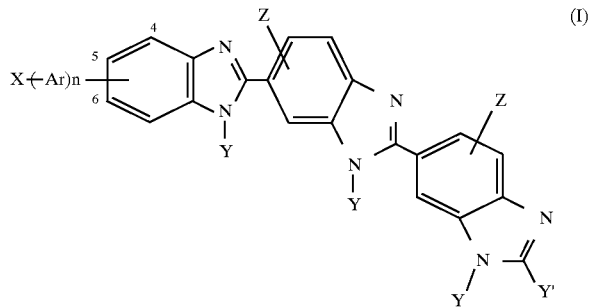

wherein Ar is aryl or a nitrogen-, sulfur- or oxygen-containing heteroaromatic group; X is H, CN, CHO, OH, acetyl, $CF_3$, $O(C_1-C_4)$alkyl, $NO_2$, $NH_2$, halogen or halo $(C_1-C_4)$alkyl; each Y is individually H, $(C_1-C_4)$alkyl or aralkyl; Y' is H, $(C_1-C_4)$ alkyl, phenyl or methoxyphenyl; each Z is individually H, $(C_1-C_4)$alkyl, halogen or halo $(C_1-C_4)$alkyl; and n is 0 or 1; or a pharmaceutically acceptable salt thereof.

Preferably, Ar is a $(C_6-C_{12})$aryl, such as phenyl, or a 5- to 12-membered heteroaryl group, most preferably a 5–6 membered heteroaryl group, comprising 1–3 N, S or non-peroxide O, wherein each N is unsubstituted or is substituted with H, $(C_1-C_4)$alkyl or benzyl. Ar can occupy the 4, 5, 6 or 7 position of the benzo ring, as shown.

As drawn, the Ar-group can occupy any position of the benzo moiety, i.e., positions 4–7, preferably the 5 position, and X can occupy any available position on Ar. Positions 4, 7 and 5, 6 are equivalent when Y is H. According to one embodiment, Ar is phenyl, and X is Cl or Br, preferably occupying the para position. As drawn, Z may occupy any position on the benzo moiety. Z is preferably H, halogen, $CH_3$ or $CF_3$.

According to another embodiment, n is 0, and X is halogen, for example, F, Br, Cl or I, preferably Cl or Br, and preferably occupies the 5-position of the benzo moiety. Y is preferably H or $CH_3$. Y' is preferably H, $CH_3$, ethyl or 4-methoxyphenyl.

While a number of known inhibitors of human topoisomerase I were found to be ineffective against a fungal topoisomerase I, including nitidine and coralyne, the compounds of formula (I) are inhibitors of fungal topoisomerase I, as demonstrated by their ability to promote DNA cleavage in the presence of Aspergillus topoisomerase I. As disclosed hereinbelow, it was unexpectedly found that the Aspergillus enzyme is completely resistant to some of the most potent human topoisomerase I poisons such as nitidine and coralyne, and to the less potent human topoisomerase I poisoning mono-benzimidazoles. Studies using yeast expressing human or yeast topoisomerase I also suggest similar resistance of the yeast topoisomerase I to these compounds. It appears that the fungal enzymes are substantially different in their drug sensitivity than their human counterpart.

Furthermore, compounds of formula (I) also are cytotoxic to mammalian tumor cells, including camptothecin-sensitive and camptothecin-resistant tumor cells and tumor cell lines exhibiting multi-drug resistance due to expression of the P-glycoprotein.

Thus, the present invention also provides pharmaceutical compositions adapted for both systemic and topical administration, comprising one or more compounds of formula (I) in combination with a pharmaceutically acceptable vehicle.

DETAILED DESCRIPTION OF THE INVENTION

The aryl groups (Ar) useful in the present compounds comprise $(C_6-C_{18})$aryl, preferably $(C_6-C_{14})$ aryl, e.g., systems containing aromatic rings, which systems comprise a total of 6 to 12 carbon atoms. Thus, as used herein, the term "aryl" includes mono- or bis-$(C_1-C_4)$alkyl-substituted aryl, such as tolyl and xylyl; ar$(C_1-C_4)$alkyl, such as benzyl or phenethyl; and alkaralkyl. Preferably aryl is pyridyl, phenyl, benzyl or naphthyl.

Heteroaromatic rings include aromatic rings containing up to 3 ring heteroatoms such as N, S or non-peroxide O, and up to 12 ring atoms. Representative aromatic rings include thiophene, benzothiophene, naphthothiophene, trianthrene, furan, benzofuran, isobenzofuran, pyran, chromene, xanthene, phenoxathiin, pyrrole, imidazole, pyrazole, pyridine, pyrazine, triazole, tetrazole, pyrazine, triazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, phenanthroline, phenazine, isothiazole, phenothiazine, oxazole, isoxazole, furazan, phenoxazine and the like. Preferred heteroaromatic rings have a 5- or 6-membered heteroaromatic ring which may or may not be fused to an aromatic ring such as a benzo ring, e.g., the preferred 2-, 3- or 4-pyridyl substituents.

The term "alkyl" includes straight-chain or branched alkyl, as well as cycloalkyl and (cycloalkyl)alkyl, e.g., methyl, ethyl, i-propyl, cyclopropyl or cyclopropylmethyl.

Pharmaceutically acceptable salts include the acid addition salts of basic NH with organic or inorganic acids, e.g., hydrochloride, carbonate, sulfate, bicarbonate, acetate, phosphate, tartarate, citrate, malate, maleate, and propionate salts, and the like.

Figure 1:
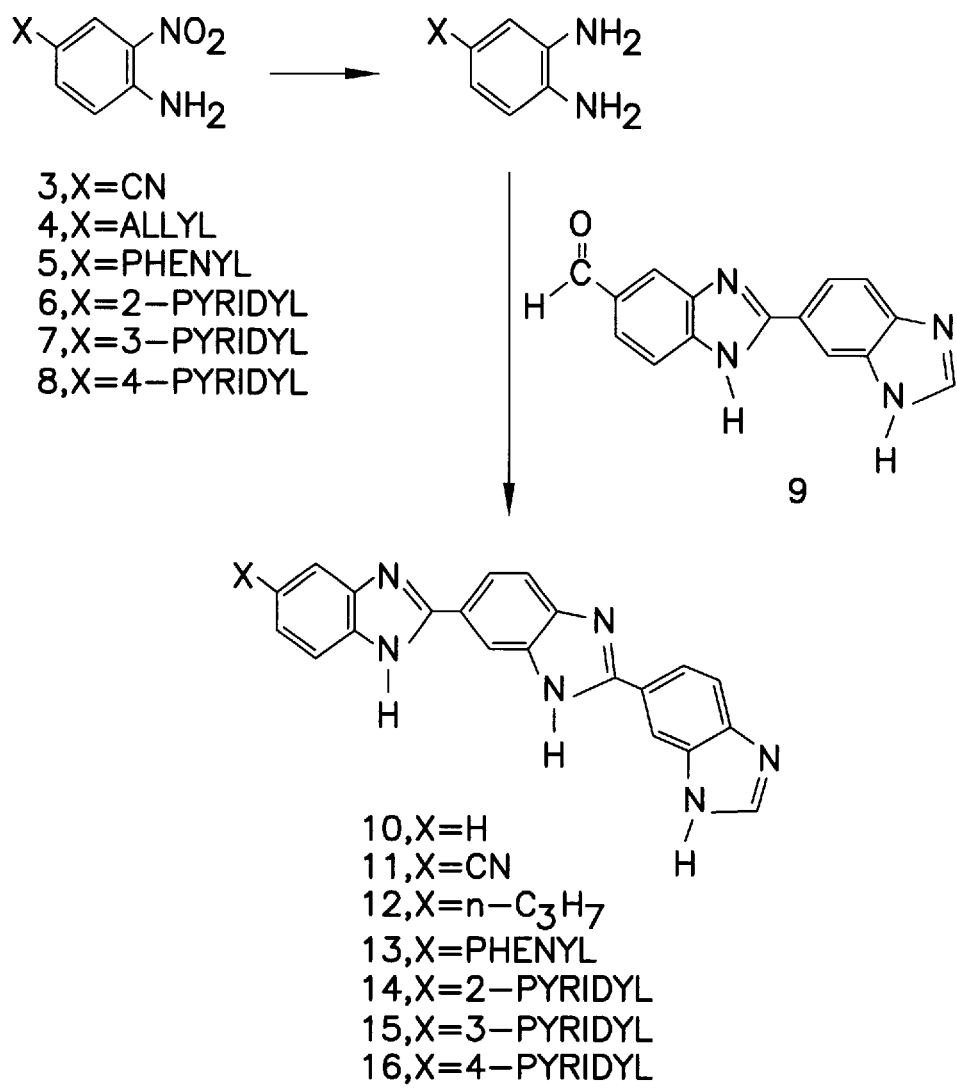
FIG. 1 is a schematic depiction of the synthesis of compounds 10–16.

The preparation of representative substituted trisbenzimidazoles is outlined in FIG. 1. With the exception of phenylenediamine which was commercially available, the appropriately substituted phenylenediamines were synthesized by catalytic hydrogenation of the respective o-nitroaniline derivatives. These phenylenediamines were then coupled with 5-formyl-2-(benzimidazo-5'-yl) benzimidazole, 9, by heating them together in nitrobenzene at 150° C. to provide the various trisbenzimidazoles, 10–16, in yields ranging from 43–96%, employing the general methodologies of M. P. Singh et al., *Chem. Res. Toxicol.*, 5, 597 (1992) and Y. Bathini et al., *Synth Comm.*, 20, 955 (1990).

Figure 2:
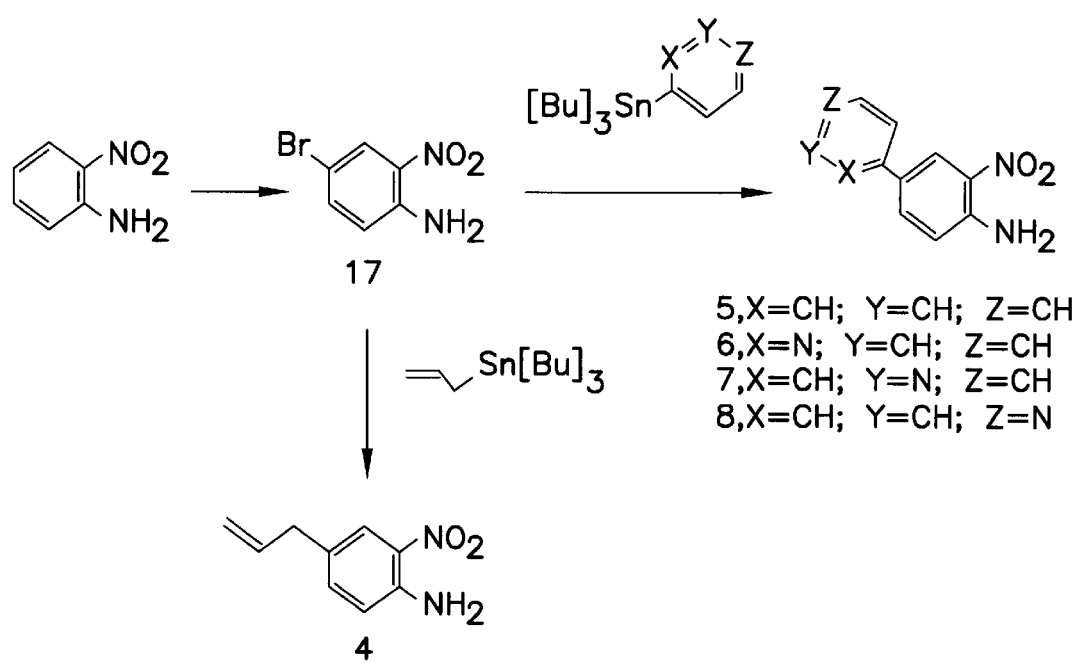
FIG. 2 is a schematic depiction of the preparation of intermediates 4–8 used to prepare compounds of the invention.

The requisite nitroanilines, as outlined in FIG. 1, with the exception of 3 which was commercially available, were synthesized from 4-bromo-2-nitroaniline, 17, Compound 17 was prepared from o-nitroaniline in good yield, 94%, using 2,4,4,6-tetrabromo-2,5-cyclohexadienone as the bromination reagent. G. J. Fox et al., *Org. Syn.*, 55, 20 (1973). While allyltributyltin and phenyltributyltin are commercially available, the pyridyltributyltin derivatives were prepared from tributyltin chloride and 2-, 3-, and 4-bromopyridine, respectively. See D. Peters et al., *Heterocyclic Chem.*, 27, 2165 (1990). These tributyltin derivatives were then coupled with 4-bromo-2-nitroaniline using $PdCl_2(PPh_3)_2$ as the catalyst in DMF as outlined in FIG. 2 to provide compounds 4, 5, 6, 7, and 8, respectively, in accord with the methodology of M. Iwao et al., *Heterocycles*, 36, 1483 (1993). This methodology can generally be applied to prepare 3-, 4-, 5- or 6-aryl- and heteroaryl-substituted 2-nitroanilines from the corresponding bromonitroanilines.

Figure 3:
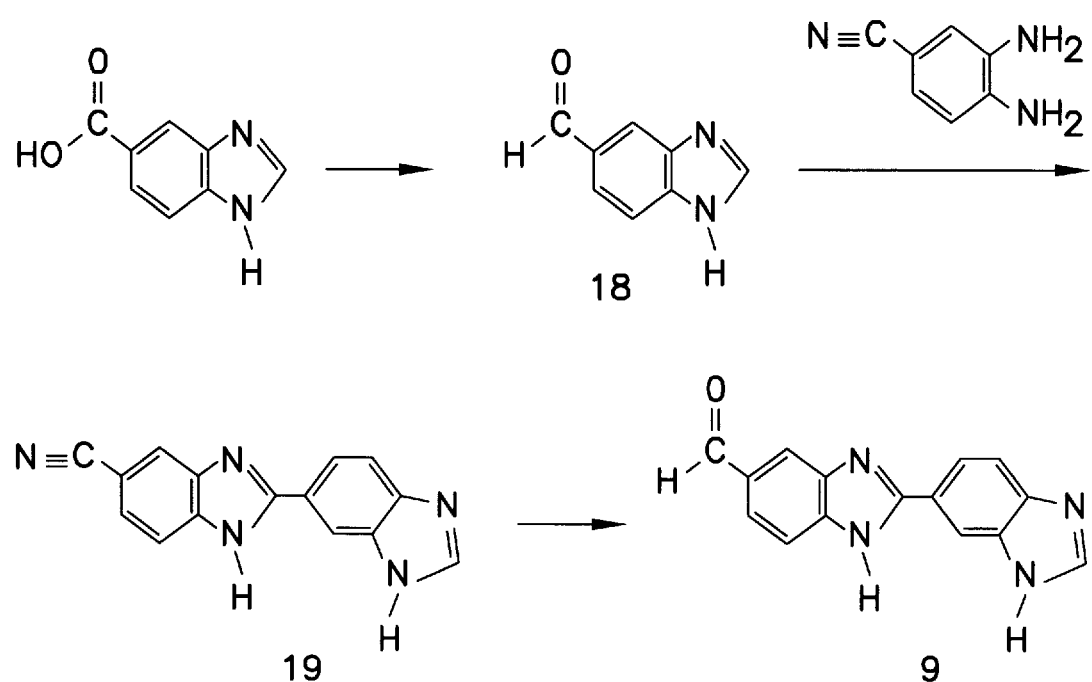
FIG. 3 is a schematic depiction of the preparation of intermediate 9.
Figure 4:
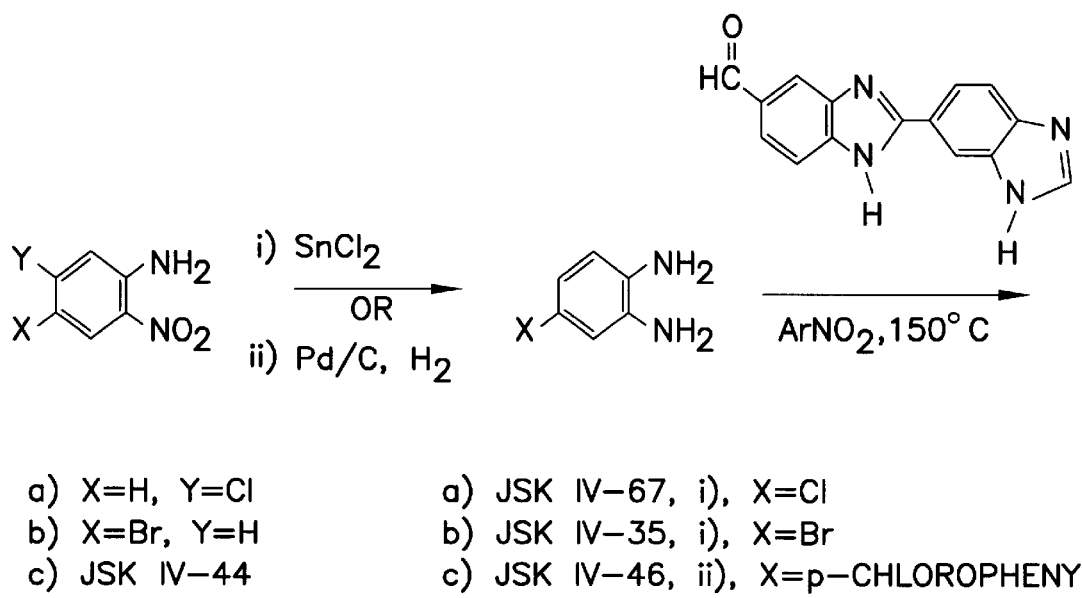
FIG. 4 is a schematic depiction of the synthesis of compounds JSKIV-68, -37 and -47.
Figure 4:
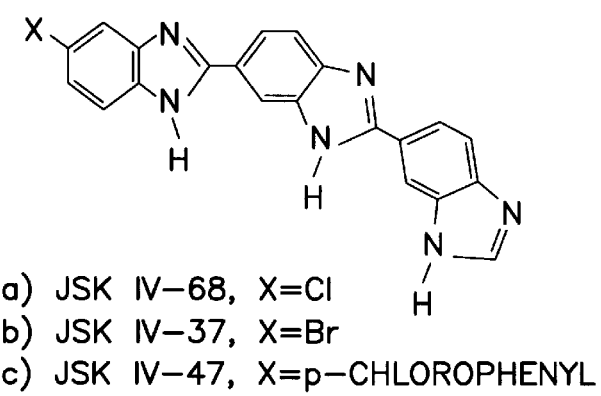
Figure 5:
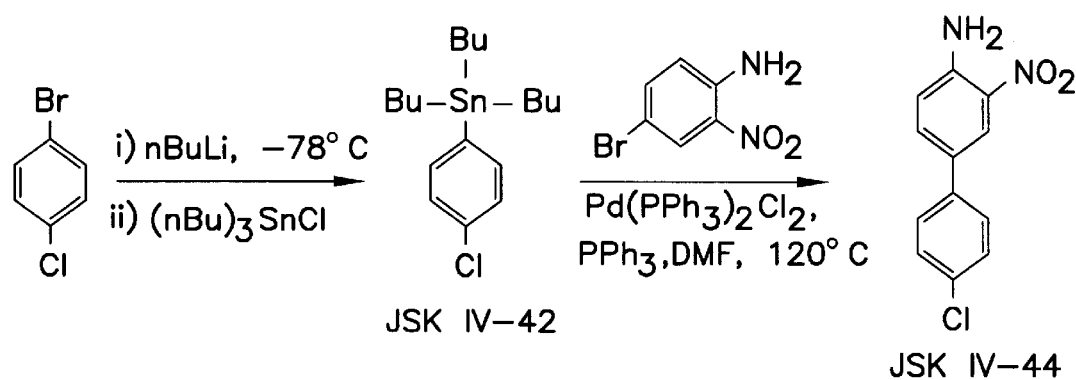
FIG. 5 is a schematic depiction of the preparation of intermediate JSKIV-44.
Figure 6:
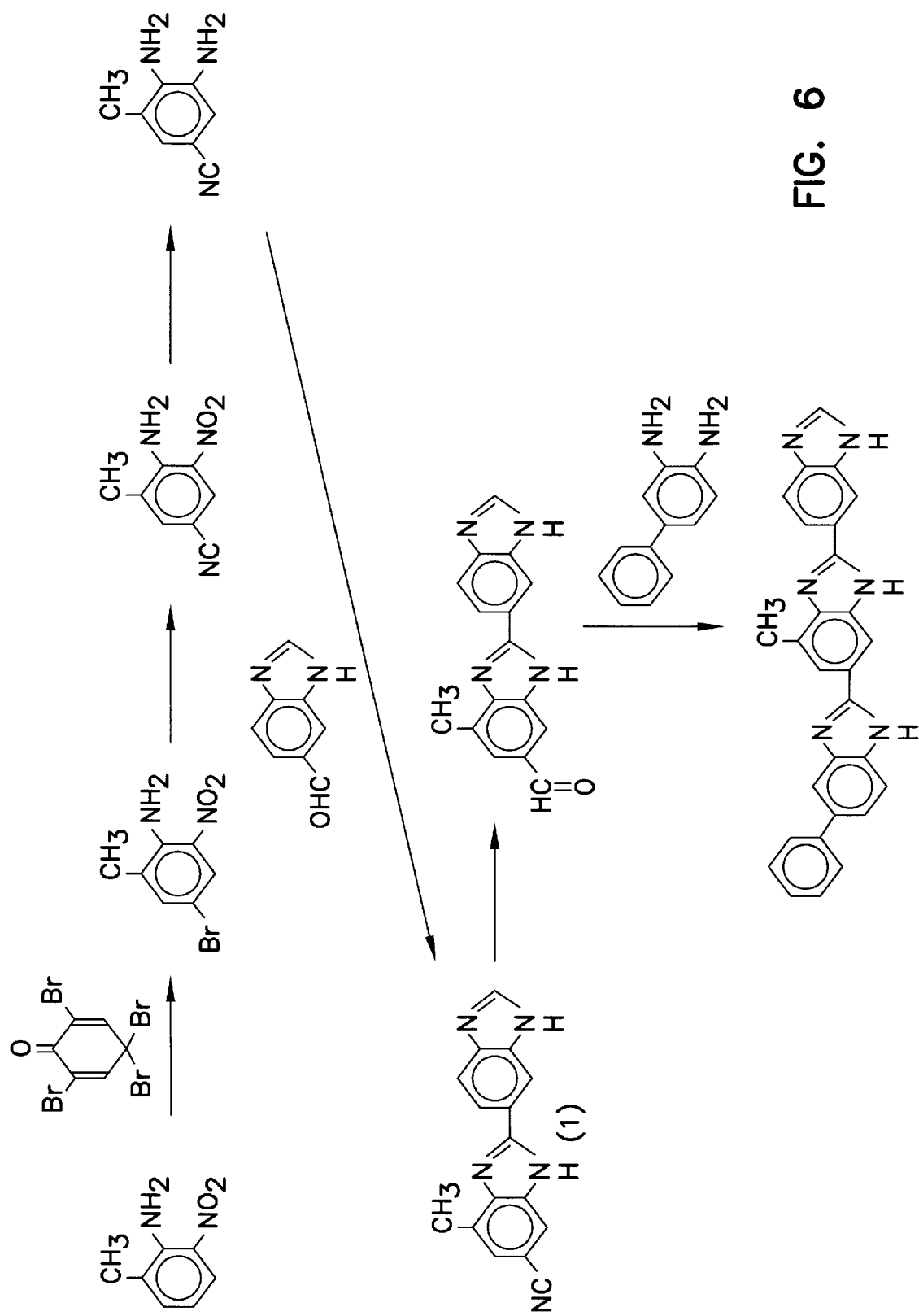
FIG. 6 is a schematic depiction of the preparation of analogs modified on the central benzimidazole moiety.
Figure 7:
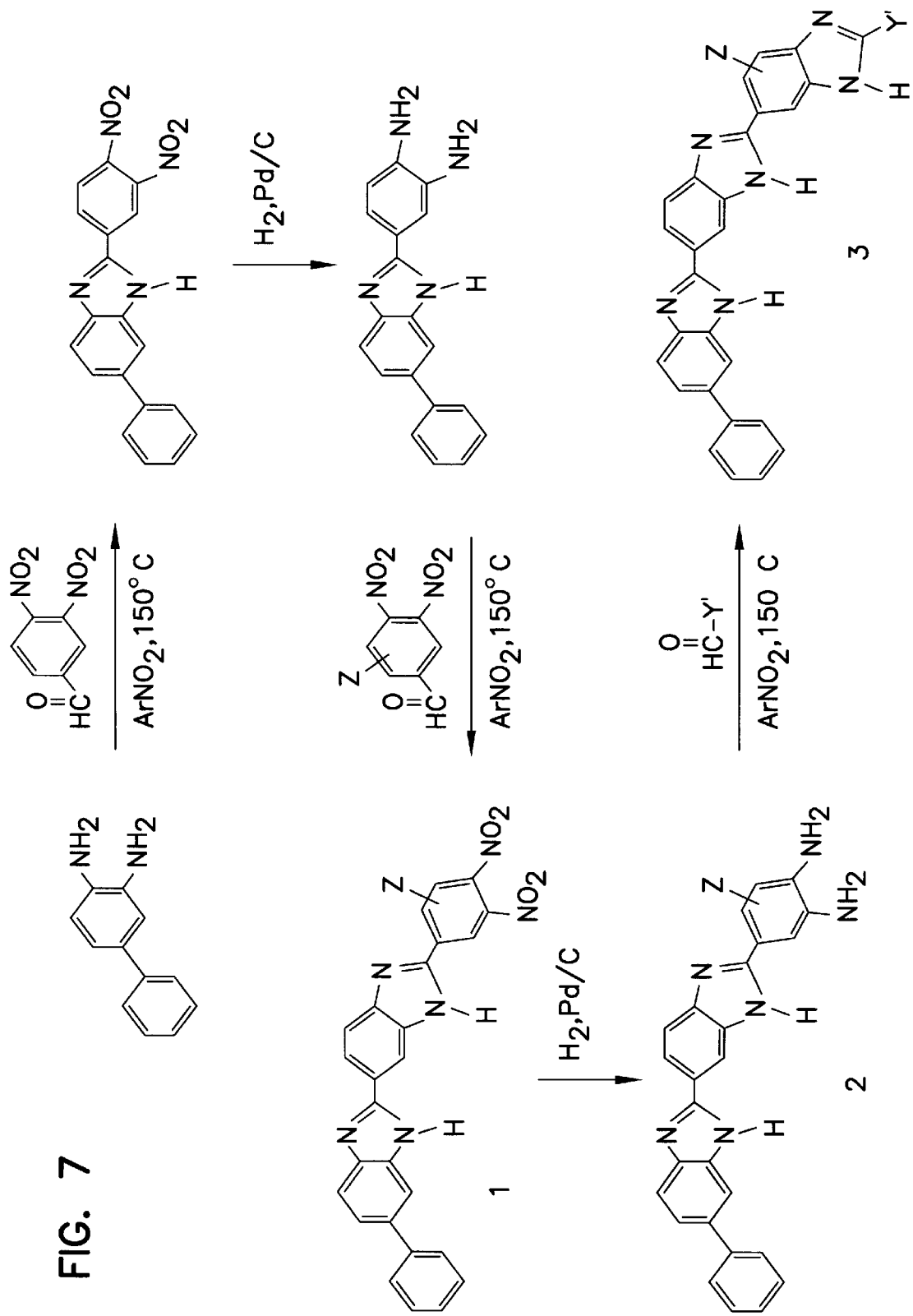
FIG. 7 is a schematic depiction of the preparation of analogs modified on the terminal benzimidazole moiety, wherein Z and Y' are as defined above.

The preparation of 5-formyl-2-(benzimidazo-5'-yl) benzimidazole, 9, was accomplished as outlined in FIG. 3. Reduction of 5-benzimidazolecarboxylic acid to 5-hydroxymethylbenzimidazole was accomplished using $LiAlH_4$. Oxidation of the resulting crude benzylic alcohol with tetrapropylammonium perruthenate (TPAP) and N-methylmorpholine N-oxide provided in two steps the desired 5-formylbenzimidazole in 32% an overall yield. See, A. Cherif et al., *J. Med. Chem.*, 35, 3208 (1992). Coupling of 5-formylbenzimidazole with 4-cyano-1,2-phenylenediamine provided 5-cyano-2-(benzimidazol-5'-yl) benzimidazole, 19 which, when treated with Ni—Al catalyst in the presence of aqueous formic acid, gave 5-formyl-2-(benzimidazol-5'-yl)benzimidazole, 9, in 65% yield. (J. R. Pipier et al., *J. Med. Chem.*, 31, 2164 (1988)).

The compounds of the present invention can be formulated as pharmaceutical compositions and administered to a mammalian host, such as an immunosuppressed human patient afflicted with a systemic or local fungal infection, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion use can include sterile aqueous solutions or dispersions or sterile powders comprising the active ingredient which are adapted for the extemporaneous preparation of sterile injectable or infusable solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersion or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be administered in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. The liquid compositions can also be employed as eyedrops, mouth washes, douches, etc. Antibacterial presaturated wipes are disclosed by Anderson (U.S. Pat. No. 4,896,768).

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Other examples of useful dermatological compositions which can be used to deliver the compounds of formula (I) to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of 1 can be determined by comparing their in vitro activity, and in vivo activity in animal models, to that of an equivalent dosage of camptothecin (see, for example, B. C. Giovanella et al., *Cancer Res,* 51, 3052 (1991)) or Hoechst 33342 (see, A. Y. Chen et al., *Cancer Res.,* 53, 1332 (1993)). Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

The present terbenzimidazoles are particularly useful to treat systemic fungal infections, or "deep mycoses." Such infections include coccidiomycosis, chromoblastomycosis, cryptococcosis, systemic moniliasis, histoplasmosis, aspergillosis, rhodotorulosis, sporotrichosis, paracoccidiodosis, phycomycosis, blastomycosis, and candidiasis. Susceptible fungi include *Candida* (*monilia*) *albicans,* which is a member of the normal flora of the mucous membranes in the respiratory, gastrointestinal, and female genital tracts. In these and other locations it may gain dominance and be associated with pathologic conditions. Sometimes it produces systemic progressive disease in debilitated or immunosuppressed patients. Candida may produce blood stream infection, thrombophlebitis, endocarditis, or infection of the eyes and other organs when introduced intravenously (tubing, needles, hyperalimentation, narcotic addiction, etc.). Other yeasts (e.g., torulopsis glabrata) may be pathogenic under similar circumstances.

The present compounds can also be used against *Cryptococcus neoformans* infections. The fungus is free-living in the soil and is found frequently in pigeon feces. In man, it can cause primary pulmonary infection that is occasionally followed by fatal meningitis.

*Blastomyces* (*Ajellomyces*) *dermatitidis* infections can also be inhibited. This fungus causes a chronic granulomatous disease, North American blastomycosis, which may be limited to the skin or lung or may be widely disseminated in the body. The present compounds can also be used against *Blastomyces brasiliensis,* an ascomycete which causes South and Central American blastomycosis (paracoccidioidal granuloma), or to treat infection with *H. capsulatum,* which usually occurs through the respiratory tract, and can lead to clinical pneumonia and protracted illness.

Infections due to *Coccidioideo immitis* can also be treated, which can cause an influenza-like illness, with fever, malaise, cough, aches, pains and sweats, and which can progress to a highly fatal form called "coccidiodal granuloma." The compounds are also effective against *Geotrichum candidum,* a yeast-like fungus which produces geotrichosis, an infection of bronchi, lungs, and mucous membranes, and *Sporothrix* (*Sporotrichum*) *schenckii,* a fungus that causes sporotrichosis, a chronic granulomatous infection of skin, lymphatics, and other tissues in animals and man. The present compounds can also be used to treat chromoblastomycosis, maduromycosis and phycomycosis, caused by *Rhizopus sp.* pr *Mucor sp.*

The present compounds are particularly effective against Aspergillus species. *Aspergillus fumigatus* and other *Aspergillus sp.* have become a frequent cause of systemic fingal infection in an altered host. Patients with leukemia or lymphoma, immunosuppressed persons (especially AIDS patients or patients undergoing organ transplants), and those receiving intensive corticosteroid therapy are particularly susceptible to aspergillosis. The portal of entry is the respiratory tract, and in most cases of aspergillosis pulmonary manifestations occur, predominantly necrotizing bronchopneumonia, hemorrhagic pulmonary infarction, or granulomas (aspergillomas).

The present compounds are also useful to inhibit the growth of fungi, including yeasts, on the skin of humans and animals such as household pets, farm animals and zoo animals. Such gram-positive microorganisms include *Propionibacterium acnes* which is the primary pathogen which causes human acne vulgaris. Mycotic skin infections of animals and humans can also be treated, including tinea capitis, tinea cruris (jock itch), tinea corporis (ringworm), tineal pedis (athlete's foot) and tinea unguium. Fungi associated with such dermatophytosis include *T. mentagrophytes, M. audevinii, T. rubrum, E. floccasum* and *M. pelineum.*

The present compounds are also effective against fungi associated with infections of the membranes of body cavities. Such infections include thrush, vaginitis and paronychia. See R. T. Yousef et al., *Mykosen*, 21, 190 (1978) and H. Gershon, *J. Pharm. Sci.*, 68, 82 (1979). The present compounds can also be used in cosmetic and skin-cleansing compositions such as soaps, shampoos, deodorants, and skin-softening lotions, where they can function as deodorants, i.e., to control odor-causing bacteria on the skin. The present compounds can also be used in shampoos, rinses, and other haircare products, to inhibit *Pityrosporum ovale* (dandruff, skin lesions in immune-suppressed subjects).

The present analogs can also be used to treat cancers known to be susceptible to topoisomerase I inhibitors, including, but not limited to, Burkitt's tumor, chronic lymphocytic leukemia, multiple myeloma, squamous cell and large cell anaplastic carcinomas, adenocarcinoma of the lung, Ewing's sarcoma, non-Hodgkins lymphoma, breast tumor, colon tumor, stomach tumor, oat-cell bronchogenic carcinoma, squamous cell carcinoma of the cervix, ovarian tumors, bladder tumors, testicular tumors, endometrial tumors, malignant melanoma and acute lymphocytic leukemia, and prostatic carcinoma. The present compounds can be administered as single agents, or in combination with other antineoplastic drugs commonly employed to treat these cancers.

The invention will be further described by reference to the following detailed examples, wherein melting points were determined with a Thomas-Hoover unimelt capillary melting point apparatus. Infrared spectral data (IR) were obtained on a Perkin-Elmer 1600 Fourier transform spectrophotometer and are reported in $cm^{-1}$. Proton ($^1$H NMR) and carbon ($^{13}$C NMR) nuclear magnetic resonance were recorded on a Varian Gemini-200 Fourier Transform spectrometer. NMR spectra (200 MHz $^1$H and 50 MHz $^{13}$C) were recorded in $CDCl_3$ (unless otherwise noted) with chemical shifts reported in δ units downfield from tetramethylsilane (TMS). Coupling constants are reported in hertz. Mass spectra were obtained from Midwest Center for Mass Spectrometry within the Department of Chemistry at the University of Nebraska—Lincoln. Combustion analyses were performed by Atlantic Microlabs, Inc., Norcross, Ga., and were with in ±0.4%. THF was freshly distilled from sodium and benzophenone prior to use. Allyltributyltin and phenyltributyltin were purchased from Aldrich Chemical Company.

Figures 8, 8A:
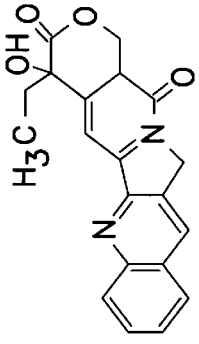
FIG. 8 summarizes the activity of various agents against human and Aspergillus topoisomerase I. The poisoning activity of various drugs against either human (H column) and Aspergillus (A column) are qualitatively indicated by a + (active) or – (inactive). DM/II/33 is only very weakly active against Aspergillus topoisomerase I and is indicated by *.
Figure 8B:
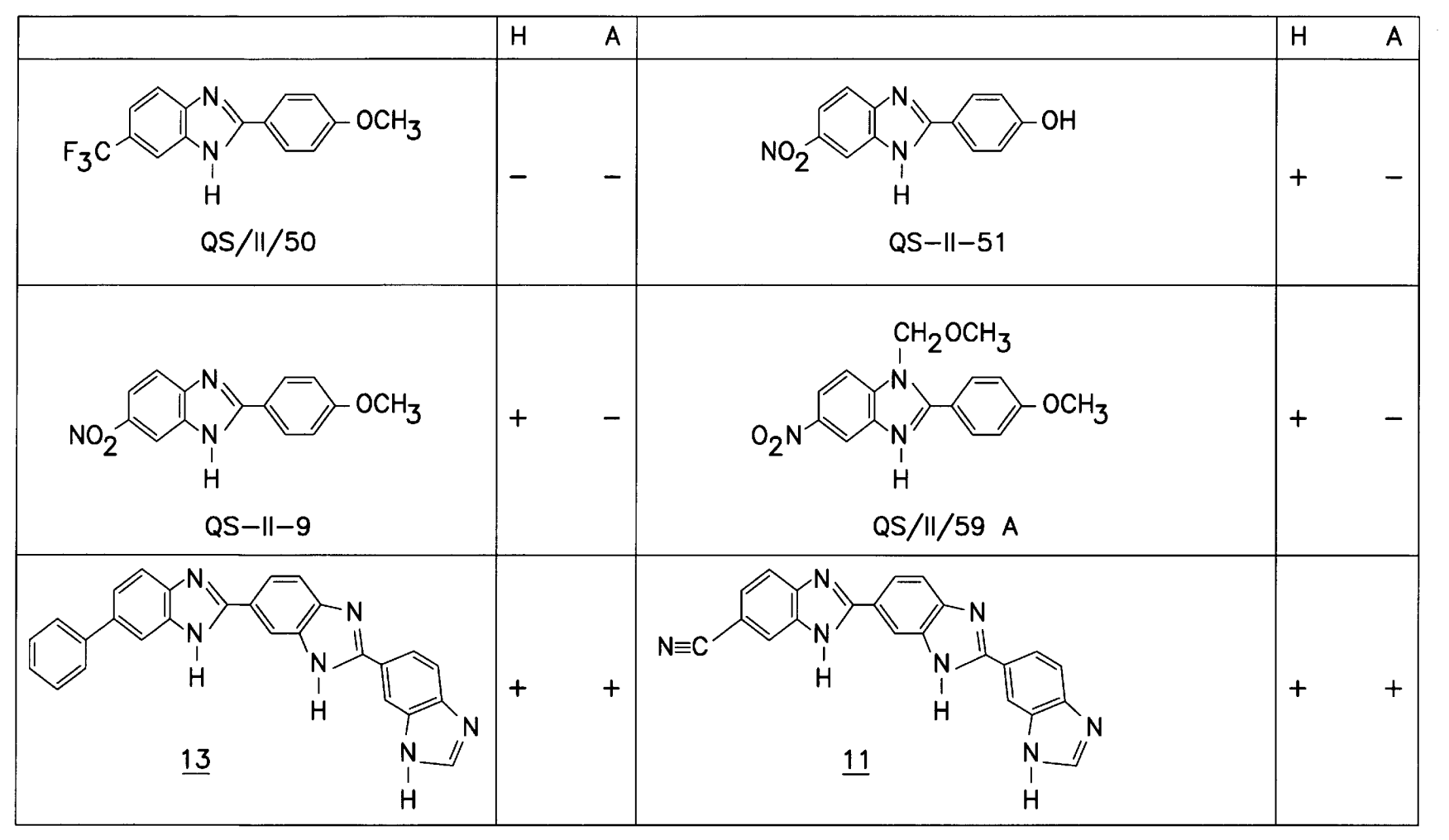

*Aspergillus nidulans* strain R21 (pabaA1, yA2) was used throughout the examples. The bibenzimidazole Hoescht dye 33342 (Ho33342), camptothecin, and berenil were purchased from Sigma Chemical Co. Mono-benzimidazoles (QS/II/9, 48, 50, 51, and 59A), terbenzimidazoles (11 and 13) and protoberberines (coralyne, DMIi33) and nitidine were synthesized as described below, and as by (Q. Sun et al., *Biorg. & Med. Chem. Lett.*, 4, 2871 (1994), and *J. Med. Chem.*, 38, 3638 (1995); Kim et al., *Biorg. & Med. Chem. Lett.*, 4, 62 (1996); *J. Med. Chem.*, 39, 992 (1996); D. Makhey et al., *Med. Chem. Res.*, 5, 1 (1995); *Biorg. & Med. Chem. Lett.*, 4 781 (1996)). (See FIG. 8 for structures.) All the drugs were dissolved in dimethyl sulfoxide (Sigma Chemical Co.) at a concentration of either 1, 5 or 10 mg/ml and kept frozen in aliquots at −20° C.

EXAMPLE 1

General Procedure for $PdCl_2(PPh_3)_2$-catalyzed Coupling Reaction of 4-Bromo-2-nitroaniline (13) with Tin Compounds (A) 4-Phenyl-2-nitroaniline (5)

A solution of 4-bromo-2-nitroaniline 17 (1.0 g, 4.67 mmol), tributylphenyl tin (2.2 g, 6.07 mmol), bis (triphenylphosphine)palladium (II) chloride (164 mg, 0.234 mmol), and triphenylphosphine (613 mg, 2.34 mmol) in DMF (15 ml) was heated under $N_2$ at 120° C. overnight. After the solution was cooled to room temperature, the reaction mixture was directly chromatographed on silica gel eluting with 2–5% EtOAc/Hexane to give 752 mg (75%) of 5 as a yellow solid: mp 169°–171° C.; IR ($CHCl_3$) 3517, 3398, 3022, 1635, 1525, 1250; $^1$H NMR δ8.38 (1H, d, J=2.2), 7.66 (1H, dd, J=8.7, 2.2), 7.59–7.54 (2H, m), 7.49–7.34 (3H, m), 6.90 (1H, d, J=8.8), 6.13 (NH, brs); $^{13}$C NMR δ144.2, 139.3, 135.0, 130.9, 129.5, 127.8, 126.8, 124.4, 119.8, 112.8; Anal. Calcd for $C_{12}H_{10}N_2O_2$: C, 67.28; H, 4.70; N, 13.08. Found: C, 67.38, H, 4.76; N, 13.01.

(B) 4-Allyl-2-nitroaniline (4)

Prepared from 4-bromo-2-nitroaniline 17 (1.70 g, 7.84 mmol) and allyltributyltin (3.38 g, 10.2 mmol) as a yellow solid in 96% yield as described above for 5: mp 29°–31° C.; IR (KBr) 3490, 3374, 1638, 1518, 1341, 1253; $^1$H NMR δ7.90 (1H, d, J=2.0), 7.19 (1H, dd, J=8.5, 2.0), 6.77 (1H, d, J=8,5), 6.05 (NH, brs), 6.00–5.80 (1H, m), 5.11 (1H, dd, =1.4, 1.4), 5.04 (1H, ddd, J=6.6, 3.0, 1.5), 3.28 (1H, d, J=6.6); $^{13}$C NMR δ143.81, 137.13, 129.34, 125.59, 119.49, 116.95, 39.18; HRMS (EI) calcd for $C_9H_{10}N_2O_2$ 178.0742, found 178.0746.

(C) 4-(2'-Pyridyl)-2-nitroaniline (6)

Prepared from 4-bromo-2-nitroaniline 17 (597 mg, 2.75 mmol) and 2-tributylstannylpyridine (1.01 g, 2.75 mmol) as a yellow solid in 52% yield as described above for 5: mp 146°–148° C.; IR ($CHCl_3$) 3516, 3397, 3020, 1634, 1524, 1341, 1250; $^1$H NMR δ8.74 (1H, d, J=2.2), 8.63 (1H, dd, J=4.9, 1.5), 8.13 (1H, dd, J=8.8, 2.1), 7.78–7.66 (2H, m), 7.20 (1H, ddd, J=4.8, 4.7, 1.9), 6.92 (1H, d, J=8.8), 6.37 (NH, brs); $^{13}$C NMR δ155.6, 150.1, 145.6, 137.4, 134.5, 129.1, 124.7, 122.4, 119.8, 119.7; Anal. Calcd for $C_{11}H_9N_3O_2$: C, 61.39; H, 4.21; N, 19.53. Found: C, 61.29; H, 4.23; N, 19.43.

(D) 4-(3'-Pyridyl)-2-nitroaniline (7)

Prepared from 4-bromo-2-nitroaniline 17 (1.42 g, 6.53 mmol) and 3-tributylstannylpyridine (3.60 g, 9.79 mmol) as a yellow solid in 32% yield as described above for 5: mp 177°–179° C.; IR ($CHCl_3$) 3515, 3399, 3052, 2983, 1638, 1524, 1341, 1259; $^1$H NMR δ8.68 (1H, d, J =1.7), 8.42 (1H, dd, J=4.8, 1.5), 8.22 (1H, d, J=2.2), 7.74 (1H, ddd, J=7.9, 2.4, 1.6), 7.50 (1H, dd, J=8.7, 2.2), 7.23 (1H, ddd, J=8.0, 4.8, 0.8), 6.92 (1H, d, J=8.8), 6.56 (NH, brs); $^{13}$C NMR δ148.7, 147.8, 145.4, 135.0, 134.4, 133.8, 126.5, 124.4, 124.0, 120.4; Anal. Calcd for $C_{11}H_9N_3O_2$: C, 61.39; H, 4.21; N, 19.53. Found: C, 61.28; H, 4.16; N, 19.40.

(E) 4-(4'-Pyridyl)-2-nitroaniline (8)

Prepared from 4-bromo-2-nitroaniline 17 (165 mg, 0.76 mmol) and 4-tributylstannylpyridine (280 mg, 0.76 mmol) as a yellow solid in 25% yield as described above for 5: mp 230°–232° C.; IR (CHCl$_3$) 3518, 3398, 3032, 1636, 1528, 1344; $^1$H NMR (CD$_3$OD) δ8.55 (2H, d, J=6.3), 8.52 (1H, d, J=2.3), 7.84 (1H, dd, J=8.9, 2.3), 7.71 (2H, d, J=6.4), 7.13 (1H, d, J=8.9); $^{13}$C NMR (CD$_3$OD) δ149.4, 133.4, 124.0, 120.7, 120.0; HRMS (EI) calcd for $C_{11}H_9N_3O_2$ 215.0695, found 215.0698.

EXAMPLE 2

5-Formyl-2-(benzimidazol-5'-yl)benzimidazole (9)

A mixture of 5-cyano-2-(benzimidazol-5'-yl) benzimidazole 19 (148 mg, 0.57 mmol), Ni—Al catalyst (500 mg), formic acid (7 ml) and water (3 ml) was heated under refluxed under N$_2$ for 4 h. The hot reaction mixture was immediately filtered through a plug of celite, and evaporated to give a yellow solid. The yellow solid was then dissolved in hot water (5 ml), and the solution was neutralized to pH 9 by 2N NaOH. The solid precipitated was collected by suction filtration and further purified by flash chromatography on silica gel (15% MeOH/EtOAc) to give 142 mg (95%) of 9 as a white solid: mp>275° C.; IR (KBr) 3106, 2835, 1685, 1618, 1432, 1293; $^1$H NMR (CD$_3$OD) δ10.01 (1H, s), 8.39 (1H, s), 8.35 (1H, s), 8.13 (1H, s), 8.06 (1H, dd, J=8.6, 1.6), 7.83 (1H, dd, J=8.4, 1.4), 7.77 (1H, d, J=8.5), 7.71 (1H, d, J=8.3); HRMS (FAB) calcd for $C_{15}H_{11}N_4O$ 263.0933, found 263.0932.

EXAMPLE 3

General Procedures for Preparing 5-substituted Trisbenzimidazoles (A) 2-[2'-(Benzimidazol-5"-yl)benzimidazol-5'-yl] benzimidazole (10)

A mixture of 5-formyl-2-(benzimidazol-5'-yl) benzimidazole 9 (121 mg, 0.46 mmol) and phenylenediamine (60 mg, 0.55 mmol) in nitrobenzene (8 ml) was heated at 150° C. under N$_2$overnight. The mixture was cooled to room temperature and chromatographed on silica gel (0–20% MeOH/EtOAc) to afford 155 mg (96%) of 10 as a solid: mp >275° C.; IR (KBr) 3400, 3157, 1630, 1542, 1438, 1294; $^1$H NMR (DMSO-d$_6$+3 drops of CF$_3$COOH) δ9.71 (1H, s), 8.75 (1H, s), 8.65 (1H, d, J=1.1), 8.48 (1H, dd, J=8.7, 1.5), 8.21 (1H, dd, J=8.6, 1.6), 8.14 (1H, d, J=8.8), 8.08 (1H, d, J=8.7), 7.90 (2H, dd, J=6.2, 3.1), 7.61 (2H, dd, J=6.1, 3.1); $^{13}$C NMR (DMSO-d$_6$+3 drops of CF$_3$COOH) δ154.4, 149.8. 133.2, 132.0, 131.7, 126.2, 125.5, 125.4, 123.9, 123.6, 116.3, 115.9, 114.23, 114.17, 114.13; HRMS (FAB) calcd for $C_{21}H_{15}N_6$ 351.1358, found 351.1367.

(B) 5-Cyano-2-[2'-(benzimidazol-5"-yl)benzimidazol-5'-yl]benzimidazole (11)

Hydrogenation of 3 (70 mg, 0.43 mmol) was accomplished at 40 psi H$_2$ at room temperature for 1 h using 10% Pd-C (30 mg) in EtOAc (10 ml). The reaction mixture was filtered and concentrated in vacuo to afford a solid. The solution of this solid and 9 (87 mg, 0.33 mmol) in nitrobenzene (5 ml) was heated at 150° C. under N$_2$ overnight. The mixture was cooled to room temperature, and chromatographed directly on silica gel (0–10% MeOH/EtOAc) to give 107 mg (86%) of 11 as a solid; mp>280° C.; IR (KBr) 3416, 3148, 2222, 1626, 1553, 1441, 1292; $^1$H NMR (DMSO-d$_6$+3 drops of CF$_3$COOH) δ8.50 (1H, s), 8.46 (1H, s), 8.40 (1H, s), 8.18–8.11 (3H, m), 7.81–7.75 (3H, m), 7.62 (1H, dd, J=8.3, 1.5); HRMS (FAB) calcd for $C_{22}H_{13}N_7$ 376.1310, found 376.1309.

(C) 5-Propyl-2-[2'-(benzimidazol-5"-yl)benzimidazol-5'-yl]benzimidazole (12)

Prepared from 4-allyl-2-nitroaniline 4 (312 mg, 1.75 mmol) and 5-formyl-2-(benzimidazol-5'-yl)benzimidazole 9 (121 mg, 0.46 mmol) in 79% yield as described above for 11: solid; mp >270° C.; IR (KBr) 3421, 3068, 2957, 1434; $^1$H NMR (DMSO-d$_6$+3 drops of CF$_3$COOH) δ9.66 (1H, s), 8.73 (1H, s), 8.59 (1H, s), 8.48 (1H, dd, J=8.7, 1.5), 8.13 (1H, dd, J=8.7, 1.4), 8.11 (1H, d, J=8.7), 8.02 ( 1H, d, J=8.5), 7.79 ( 1H, d, J =8.4), 7.66 (1H, s), 7.45 (1H, dd, J=8.5, 1.3), 2.80 (2H, t, J=7.0), 1.70 (2H, m), 0.96 (3H, t, J=7.2); $^{13}$C NMR (DMSO-d$_6$+3 drops of CF$_3$COOH) δ153.84, 149.74, 141.64, 141.01, 139.37, 133.10, 132.26, 131.99, 130.34, 127.08, 126.26, 125.14, 141.64, 141.01, 139.37, 133.10, 132.26, 131.99, 130.34, 127.08, 126.26, 125.14, 122.91, 117.52, 116.32, 116.06, 115.76, 113.78, 112.99, 37.45, 24.73, 13.74.

(D) 5-Phenyl-2-[2'(benzimidazol-5"-yl)benzimidazol-5'-yl]benzimidazole (13)

Prepared from 4-phenyl-2-nitroaniline 5 (247 mg, 1.15 mmol) and 5-formyl-2-(benzimidazol-5'-yl)benzimidazole 9 (201 mg, 0.77 mmol) in 89% yield as described for 11: solid; mp 262°–164° C. dec; IR (KBr) 3402, 3104, 1627, 1552, 1442, 1290; $^1$H NMR (DMSO-d$_6$+3 drops of CF$_3$COOH) δ9.66 (1H, s), 8.74 (1H, s), 8.65 (1H, s), 8.50 (1H, dd, J=8.8, 1.1), 8.21 (1H, dd, J=8.7, 1.4), 8.12 (1H, d, J=8.8), 8.06 (1H,s), 8.05 (1H, d, J=8.4), 7.97 (1H, d, J=8.7), 7.89 (1H, dd, J=8.7, 1.5), 7.80 (2H, d, J=7.0), 7.61–7.47 (3H, m); HRMS (FAB) calcd for $C_{27}H_{19}N_6$ 427.1671, found 427.1666.

(E) 5-(2-Pyridyl)-2-[2'-(benzimidazol-5"-yl)benzimidazol-5'-yl]benzimidazole (14)

Prepared from 4-(2'-pyridyl)-2-nitroaniline, 6 (110 mg, 0.50 mmol), and 5-formyl-2-(benzimidazol-5'-yl) benzimidazole 9 (51 mg, 0.25 mmol) in 84% yield as described above for 11: solid; mp >275° C.; IR (KBr) 3411, 3157, 1630, 1593, 1432; $^1$H NMR (CD$_3$OD) δ8.59 (1H, d, J=4.8), 8.35 (1H, s), 8.31–8.25 (2H, m), 8.10 (1H, s), 8.04–7.94 (2H, m), 7.85–7.77 (3H, m), 7.72 (1H, d, J=8.6), 7.68 (1H, d, J=8.7), 7.64 (1H, d, J=8.7), 7.30 (1H, m); HRMS (FAB) calcd for $C_{26}H_{18}N_7$ 428.1624, found 428.1611.

(F) 5-(3-Pyridyl)-2-[2'-(benzimidazol-5"-yl)benzimidazol-5'-yl]benzimidazole (15)

Prepared from 4-(3'-pyridyl)-2-nitroaniline 7 (183 mg, 0.85 mmol) and 5-formyl-2-(benzimidazol-5'-yl) benzimidazole 9 in 46% yield as described above for 11: solid; mp >275 ° C.; IR (KBr) 3400, 3070, 2836, 1438, 1289; $^1$H NMR (CD$_3$OD) δ8.83 (1H, d, J=1.6), 8.49 (1H, dd, J=4.9, 1.5), 8.38 (1H, d, J=1.1), 8.31 (1H, d, J=1.1), 8.29 (1H, s), 8.11 (1H, ddd, J=8.0, 2.3, 1.6), 8.05 (1H, dd, J=8.5, 1.6), 8.00 (1H, dd, J=8.5, 1.6), 7.81 (1H, d, J=1.1), 7.77–7.68 (3H, m), 7.55–7.47 (2H, m); HRMS (FAB) calcd for $C_{26}H_{18}N_7$ 428.1624, found 428.1612.

(G) 5-(4-Pyridyl)-2-[2'-(benzimidazol-5"-yl)benzimidazol-5'-yl]benzimidazole (16)

Prepared from 4-(4'-pyridyl)-2-nitroaniline 8 (35 mg, 0.16 mmol) and 5-formyl-2-(benzimidazol-5'-yl)benzimidazole 9 (50 mg, 0.19 mmol) in 43% yield as described above for 11: solid; mp >280 ° C.; IR (KBr) 3411, 3118, 1600, 1552, 1439, 1290; $^1$H NMR (CD$_3$OD) δ8.51 (2H, d, J=6.2), 8.33 (1H, d, J=1.1), 8.27 (1H, s), 8.25 (1H, d, J=1.1), 8.01 (1H, dd, J=8.6, 1.7), 7.96 (1H, dd, J=8.9, 2.0), 7.87 (1H, d, J=1.0), 7.74–7.56 (6H, m); HRMS (FAB) calcd for $C_{26}H_{18}N_7$ 428.1624, found 428.1625.

EXAMPLE 4

4-Bromo-2-nitroaniline (17)

A solution of 2-nitroaniline (5 g, 36.2 mmol) in CH$_2$Cl$_2$ (100 ml) was cooled to −10° C., and treated by 90% 2,4,4,6-tetrabromo-2,5-cyclohexadienone (19.8 g, 43.5 mmol) in 5 portions. The mixture was stirred at −10° C.–0° C. for 1 hr. After being warmed to room temperature, the reaction mixture was washed by 2N NaOH (60 ml) and brine (50 ml), dried over Na$_2$SO$_4$ and evaporated. Flash chromatography on silica gel (5% EtOAc/Hexane) gave 7.40 g (94%) of 17 as a yellow solid: mp 109–110 (lit. mp 112°–113° C.); $^1$H NMR δ8.27 (1H, d, J=2.3), 7.43 (1H, dd, J=8.9, 2.4), 6.73 (1H, d, J=8.8), 6.09 (NH, brs).

EXAMPLE 5

5-Formylbenzimidazole (18)

A suspension of 5-benzimidazolecarboxylic acid (1.57 g, 9.7 mmol) in dry THF (50 ml) was cooled to −78° C. under N$_2$, and treated with LiAlH$_4$ (736 mg, 19.4 mmol). After the addition, the mixture was allowed to warm slowly to room temperature and then stirred at r.t. overnight. The mixture was quenched by MeOH and H$_2$O cautiously, and passed through a short silica gel column eluting with 10% MeOH/EtOAc. The eluate was concentrated to give 876 mg crude alcohol as a solid. The crude alcohol (876 mg) was dissolved in a mixture of DMF (3 ml), THF (10 ml) and CH$_2$Cl$_2$ (40 ml). 4-Methylmorpholine N-oxide (2.25 g, 19.2 mmol), 4 Å molecular sieves (5 g), and TPAP (169 mg, 0.48 mmol) were subsequently added to the crude alcohol solution. The mixture was stirred at room temperature overnight, and filtered through a pad of silica gel eluting with 10% MeOH/EtOAc. The elute was concentrated and further purified by flash chromatography on silica gel eluting with 0–10% MeOH/EtOAc to give 452 mg (32%, 2 steps) of 17 as a white solid: mp 164°–166° C.; IR (KBr) 3087, 2818, 1690, 1292; $^1$H NMR (CD$_3$OD) δ9.95 (1H, s), 8.34 (1H, s), 8.08 (1H, d, J=1.5), 7.74 (1H, dd, J=8.4, 1.5), 7.63 (1H, d, J=8.4); $^{13}$C NMR (CD$_3$OD) δ194.2, 146.0, 143.0, 139.8, 133.6, 124.9, 120.7, 116.6; Anal. Calcd for C$_8$H$_6$N$_2$O: C, 65.75; H, 4.14; N, 19.17. Found: C, 65.60; H, 4.17; N, 19.08.

EXAMPLE 6

5-Cyano-2-(benzimidazol-5'-yl)benzimidazole (19)

A mixture of 5-formylbenzimidazole 18 (211 mg, 1.44 mmol) and 4-cyano-1,2-phenylenediamine (230 mg, 1.73 mmol) in nitrobenzene (10 ml) was heated at 150° C. under N$_2$ overnight. The mixture was cooled to room temperature and directly chromatographed on silica gel eluting with 0–15% MeOH/EtOAc to give 244 mg (65%) of 18 as a solid: mp >270° C.; IR (KBr) 3110, 2826, 2224, 1627, 1426, 1294; $^1$H NMR (CD$_3$OD) δ8.41 (1H, s), 8.33 (1H, s), 8.07 (1H, dd, J=8.6, 1.5), 7.98 (1H, s), 7.78 (1H, d, J=8.4), 7.73 (1H, d, J=8.4), 7.56 (1H, dd, J=8.4, 1.5); $^{13}$C NMR (DMSO-d$_6$+3 drops of CF$_3$COOH) δ153.4, 140.4, 138.3, 132.9, 131.6, 127.0, 125.8, 125.3, 120.8, 119.8, 116.0, 115.8, 113.9, 105.5; HRMS (FAB) calcd for C$_{15}$H$_{10}$N$_5$ 260.0936, found 260.0935.

EXAMPLE 7

(A) 5-Bromo-2-[2'-(benzimidazol-5"-yl)benzimidazol-5'-yl]-benzimidazole (JSK IV-37)

A mixture of 5-formyl-2-(benzimidazol-5'-yl)benzimidazole (118.8 mg, 0.45 mmol) and 5-bromophenylenediamine (169.6 mg, 0.90 mmol) in nitrobenzene (5 mL) was heated at 150° C. under N$_2$ overnight. The mixture was cooled to room temperature and chromatographed using 0–10% methanol/ethyl acetate to afford 127.3 mg (66%) of brownish yellow solid: mp>280° C.; IR (KBr) 3101, 1626, 1547, 1440; $^1$H NMR (DMSO-d$_6$) δ7.34 (dd, 1H, J=7.0, 2.0), 7.57 (d, 1H, J=9.0), 7.71–7.80 (m, 3H), 8.04–8.18 (m, 2H), 8.39 (s, 2H), 8.50 (s, 1H); $^{13}$C NMR (DMSO-d$_6$+3 drops CF$_3$COOH) δ114.1 115.8, 116.2, 116.4, 117.0, 118.6, 123.5, 125.3, 126.2, 128.7, 128.9, 131.8, 132.0, 132.3, 133.1, 134.4, 138.3, 140.6, 151.1, 153.4.

(B) 5-Chloro-2-[2'-(benzimidazol-5"-yl)benzimidazol-5'-yl]-benzimidazole (JSK IV-68)

A mixture of 5-formyl-2-(benzimidazol-5'-yl)benzimidazole (160 mg, 0.61 mmol) and 5-chlorophenylenediamine (174 mg, 1.22 mmol) in nitrobenzene (5 mL) was heated at 150° C. under N$_2$ overnight. The mixture was cooled to room temperature and chromatographed using 0–10% methanol/ethyl acetate to afford 167 mg (71%) of brownish yellow solid: mp>280° C.; IR (KBr) 3103, 2826,1427, 1293; $^1$H NMR (DMSO-d$_6$) δ7.24 (dd, 1H, J=8.5, 2.0), 7.60–7.81 (m, 4H), 8.07–8.17 (m, 2H), 8.40 (s, 2H), 8.50 (s, 1 H); $^{13}$C NMR (DMSO-d$_6$+3 drops CF$_3$COOH) δ114.3, 114.4, 115.3, 115.5, 115.6, 116.2, 118.5, 123.1, 125.4, 125.5, 125.6, 129.4, 132.4, 132.9, 133.0, 135.2, 138.9, 140.9, 151.8, 153.5.

(C) 5-(p-Chlorophenyl)-2-[2'-(benzimidazol-5"-yl)benzimidazol-5'-yl]-benzimidazole (JSK IV-47)

A mixture of 5-formyl-2-(benzimidazol-5'-yl)benzimidazole (99 mg, 0.38 mmol) and 5-(p-chlorophenyl)phenylenediamine (154 mg, 0.71 mmol) in nitrobenzene (5 mL) was heated at 150° C. under N$_2$ overnight. The mixture was cooled to room temperature and chromatographed using 0–10% methanol/ethyl acetate to afford 85 mg (49%) of brownish yellow solid: mp>280° C.; IR (KBr) 3046, 2820, 1426, 1282; $^1$H NMR (DMSO-d$_6$+3 drops CF$_3$COOH) δ7.56 (d, 2H, J=8.5), 7.82 (d, 2H, J=8.5), 7.88–8.21 (m, 6H), 8.48 (d, 1H, J=8.8), 8.63 (s, 1H) 8.72 (s, 1H), 9.69 (s, 1H); $^{13}$C NMR (DMSO-d$_6$+3 drops CF$_3$COOH) δ111.8, 113.8, 114.7, 115.8, 116.1, 117.7, 123.0, 124.1, 125.2, 125.3, 129.2, 129.3, 131.9, 132.1, 133.0, 133.1, 137.2, 138,5, 139.3, 141.6, 150.8, 153.8.

(D) 4-Bromophenylenediamine (JSK IV-35)

To 2-nitro-4-bromoaniline (340 mg, 1.57 mmol) in absolute ethanol (20 mL) was added SnCl$_2$ (1.50g, 7.91 mmol) and refluxed overnight. The reaction mixture was then basified to pH 11 with 2N NaOH and extracted with ether to give 275 mg (94%) of product. This product was used without further purification for the synthesis of JSK IV-37.

(E) 4-Chlorophenylenediamine (JSK IV-67)

To 2-nitro-5-chloroaniline (304 mg, 1.76 mmol) in absolute ethanol (20 mL) was added SnCl$_2$ (1.68g, 8.86 mmol) and refluxed overnight. The reaction mixture was then basified to pH 11 with 2N NaOH and extracted with ether to give 250 mg (quantitative yield) of product. This product was used without further purification for the synthesis of JSK IV-68.

(F) p-Chlorotributylphenyltin (JSK IV-42)

4-Bromochlorobenzene (3.2 g, 16.62 mmol) was dissolved in dry THF (20 mL). After bringing the reaction temperature down to −78° C. with an acetone/dry ice bath, nBuLi (15.58 mL, 1.6M, 1.5 equiv.) was added slowly and stirred at −78° C. for 30 min. Tributyltinchloride (6.77 mL, 1.5 equiv.) was added and stirred overnight while bringing the reaction to room temperature. Reaction mixture was quenched by stirring the reaction flask open in air for 1 hour after which THF was rotavaporated off. Product was obtained as an oil (7.35g, 97%) after passing the mixture through a quick silica gel column eluting with 100% hexanes.

(G) 2-Nitro-5-(p-chlorophenyl)aniline (JSK IV-44)

To JSK IV-42 (2.02 g, 5.04 mmol) and 2-nitro-4-bromoaniline (730 mg, 3.36 mmol) in DMF (18 mL) was added $Pd(PPh_3)_2Cl_2$ (117.9 mg, 0.17 mmol) and $PPh_3$ (440.2 mg, 1.70 mmol) and heated at 120° C. overnight. DMF was rotavaporated off and the mixture was separated on a silica gel column eluting with 5–10% ethylacetate/hexanes to give 270 mg (32%) of reddish solid.

(H) 4-(p-Chlorophenyl)phenylenediamine (JSK IV-46)

JSK IV-44 (190 mg, 0.77 mmol) was dissolved in ethyl acetate (100 mL) and after adding 10% Pd—C (40 mg) was reduced by hydrogenation (45 psi). Product (quantitative yield) was used in JSK IV-47 without further purification.

EXAMPLE 8

Bioassays

A. Topoisomerase I-Mediated DNA Cleavage Assays

DNA topoisomerase I was purified from calf thymus gland as reported previously by B. D. Halligan et al., *J. Biol. Chem.*, 260, 2475 (1985).

Plasmid YEpG was also purified by the alkali lysis method followed by phenol deproteination and CsCl/ethidium isopycnic centrifugation as described by T. Maniatis et al., *Molecular Cloning, A Laboratory Manual*, Cold Spring Harbor Labs, N.Y. (1982) at pages 149–185. The end-labeling of the plasmid was accomplished as previously described by L. F. Liu et al., *J. Biol. Chem.*, 258, 15365 (1983). The cleavage assays were performed as previously reported by A. Y. Chen et al., *Cancer Res.*, 53, 1332 (1993). Human topoisomerase I was isolated as a recombinant fusion protein using a T7 expression system.

B. Cytotoxicity Assay

The cytotoxicity was determined using the as MTT-microtiter plate tetrazolinium cytotoxicity assay (MTA) following the procedures of F. Denizot et al., *J. Immunol. Methods*, 89, 271 (1986); J. Carmichael et al., *Cancer Res*, 47, 936 (1987) and T. J. Mosmann et al., *Immunol. Methods*, 65, 55 (1983). The human lymphoblast RPMI 8402 and its camptothecin-resistant variant cell line, CPT-K5 were provided by Dr. Toshiwo Andoh (Aichi Cancer Center Research Institute, Nagoya, Japan). See, for example, T. Andoh et al., *Adv. Pharmacol.*, 29B, 93 (1994). The cytotoxicity assay was performed using 96-well microtiter plates. Cells were grown in suspension at 37 ° C. in 5% $CO_2$ and maintained by regular passage in RPMI medium supplemented with 10% heat inactivated fetal bovine serum, L-glutamine (2 mM), penicillin (100 U/ml), and streptomycin (0.1 mg/ml). For determination of $IC_{50}$, cells were exposed continuously with varying concentrations of drug concentrations and MTT assays were performed at the end of the fourth day.

The drug sensitive human epidermoid carcinoma KB3-1 cell line (S. Aliyama et al., *Somatic Cell Mol. Genet.*, 11, 117 (1985)) and its vinblastine-selected multidrug-resistant variant KBV-1 cells (D. W. Shen et al., *Science*, 32, 643 (1986)) were provided by Dr. Michael Gottesmann (National Cancer Institute, Bethesda, Md.). These cells were grown as monolayer cultures at in 5% $CO_2$ and maintained by regular passage in Dulbecco's minimal essential medium supplemented with 10% heat inactivated fetal bovine serum. KBV-1 cells were similarly maintained except they were grown in the presence of 1 µg/ml vinblastine.

C. Results

As shown on Table 1, comparison of compounds 10–16 and halo analogs JSKIV-37, 47 and 68 with Hoechst 33342 (1) as inhibitors of topoisomerase I demonstrated that several of these trisbenzimidazoles had similar or greater potency.

TABLE 1

Topoisomerase I-mediated DNA Cleavage and Cytotoxicity of Bis- and Trisbenzimidazoles

| Compound | Topo I-mediated DNA cleavage[b] | Cytotoxicity $IC_{50}$[a] (µM) Cell Lines | | | |
|---|---|---|---|---|---|
| | | RPMI | CPT-K5 | KB3-1 | KBV-1 |
| Hoechst 33342 | 1 | 0.03 | 0.9 | 0.01 | 1.2 |
| 10 | 1.1 | 14 | 28 | N.D. | N.D. |
| 11 | 1 | >25[c] | >25[c] | N.D. | N.D. |
| 12 | 100 | 7.6 | 20 | N.D. | N.D. |
| 13 | 2 | 0.09 | 0.58 | 0.58 | 0.35 |
| 14 | 3.3 | 0.16 | 5.8 | 0.05 | 0.09 |
| 15 | 2 | 0.035 | 2.5 | 0.02 | 0.02 |
| 16 | 2 | 0.035 | 2.5 | 0.02 | 0.01 |
| 19 | 1000 | >25[c] | N.D. | N.D. | N.D. |
| JSKIV-37 | 1 | 1.40 | 1.40 | | |
| JSKIV-47 | 10 | 0.09 | 0.20 | | |
| JSKIV-68 | 1 | 1.04 | 0.65 | | |

[a]$IC_{50}$ has been calculated after 4 days of continuous drug exposure. N.D. = Not determined.
[b]Topoisomerase I cleavage values are reported as REC, Relative Effective Concentration, i.e. concentrations relative to Hoechst 33342, whose value is arbitrarily assumed as 1, that are able to produce the same cleavage on the plasmid DNA in the presence of calf thymus topoisomerase I. Cleavage is calculated from the intensity of the strongest Hoechst specific band.
[c]No indication of cytotoxicity were considered indicative of $IC_{50}$ values substantially greater than the highest doses assayed.

While 10 and 11 exhibited similar potency in their inhibition of topoisomerase I as observed with Hoechst 33342, both of these compounds failed to exhibit significant cytotoxicity towards the human lymphoblast cell line, RPMI 8402. However, this may be due to the inability of the pure compound to penetrate the target cells, which may be overcome by selection of a suitable carrier, such as liposomes. The 5-phenyl substituted trisbenzimidazole, 13, was approximately one-half as potent as Hoechst 33342 as a topoisomerase I inhibitor. In contrast to 10 and 11, however, it had significant cytotoxicity towards the human lymphoblast cell line, RPMI 8402 cells. As observed with Hoechst 33342, 13 was also effective against camptothecin-resistant CPT-K5 cells. The relative resistance of Hoechst 33342 and 13, expressed as the ratio of the $IC_{50}$ values of the resistant verses the drug sensitive cell line, is approximately 30 fold as compared to the relative resistance of camptothecin which is 2,500 fold, as reported by A. Y. Chen et al., *Cancer Res.*, 53, 1332 (1993). A similar effect was observed in another pair of cell lines; 13 has an $IC_{50}$ of 0.015 µg/ml in the human ovarian tumor cell line, A2780, relative to an $IC_{50}$ of 0.03 µg/ml in CPT-2000, a variant of A2780 selected for camptothecin-resistance and known to contain a mutant camptothecin-resistant topoisomerase I. The 5-n-propyl trisbenzimidazole derivative, 12, was much less active than either 10, 11, or 13 as an inhibitor of topoisomerase I. Its weak activity as a topoisomerase I inhibitor correlated with its weak cytotoxicity. The activity of several of these compounds were also evaluated using recombinant human topoisomerase I. Several of these analogs induced similar DNA cleavage in the presence of human topoisomerase I as compared to that observed with topoisomerase I isolated from calf thymus.

The cytotoxic activity of Hoechst 33342 and 13 was also evaluated against KB 3-1 and KB V-1 cells. The primary difference between these cell lines is in the degree to which human MDR1 (P-glycoprotein) is expressed. Recent studies have demonstrated that antineoplastic agents which are cationic at physiological pH are more likely to serve as substrates for MDR1 and, therefore, are likely to be less effective against cells that overexpress P-glycoprotein. In view of the fact that Hoechst 33342 is extensively protonated at physiological pH, it is not surprising that the $IC_{50}$ differs by approximately two-orders of magnitude for KB 3-1 as compared to KB V-1 cells, as reported by A. Y. Chen et al., Adv. Pharmacol., 245, 29B (1994). In contrast to Hoechst 33342, there is little difference between the $IC_{50}$ values observed for 13 in these two cell lines. Thus, 13 appears not to be a substrate for human MDR1. This data indicate that these trisbenzimidazole derivatives may have significant chemotherapeutic advantages as compared to Hoechst 33342 or pibenzimol (Hoechst 33258), 2'-(4-hydroxyphenyl)-5-(4-methyl-1-piperazinyl)-2,5'-bi-1H-benzimidazole.

These data indicate that substitution of these trisbenzimidazole with a 5-Ar substituent can yield derivatives which are active as topoisomerase I inhibitors and cytotoxic to tumor cells. Trisbenzimidazoles substituted at the 5- position with either a 2-, 3-, or 4-pyridyl group, 14–16, were evaluated for their potency as topoisomerase I inhibitors and for cytotoxicity as summarized in Table 1. These analogs, similar to 13, have activity as topoisomerase I inhibitors. The 3- and 4-pyridyl analogs, 15 and 16, are somewhat more active than the 2-pyridyl derivative, 14, as topoisomerase I inhibitors as well as cytotoxic agents. As was observed with 13, these pyridyl-substituted tribenzimidazoles had similar cytotoxicity to KB 3-1 cells as well as to KB V-1 cells which overexpress MDR1. A principal advantage of these heteroaryl substituted trisbenzimidazoles as compared to Hoechst 33342 is their efficacy against cell lines which express MDR1.

EXAMPLE 9

Partial Purification of Topoisomerase I from *Aspergillus nidulans*

Two liters of YG medium (0.5% yeast extract and 2% glucose) were inoculated with approximately $5 \times 10^8$ conidia/ml. After 16 hours of growth at 37° C., the mycelia were collected, washed with Buffer I (50 mM Tris-HCl, pH 7.7, 1 mM EDTA, 1 mM EGTA, 10% glycerol, 1 mM phenylmethylsulfonyl fluoride and 1 mM 2-mercaptoethanol), and quickly chilled in liquid nitrogen. The frozen mycelia (approximately 20 grams) were ground to powder and resuspended in 300 ml of Buffer I. The lysate was centrifuged at 10K rpm in a Sorval HB3 Rotor for 15 minutes to remove cell debris. The supernatant was made 6% in polyethylene glycol (v/v) and 1M NaCl. After one hour on ice with gentle stirring, the solution was centrifuged at 14K rpm in a Sorvall Rotor for 30 minutes to remove nucleic acids.

Subsequent steps in purification were the same as described previously for purification of recombinant human DNA topoisomerase I (B. Gatto et al., Cancer Res., 56, 2795 (1996)). Briefly, the supernatant was chromatographed directly onto a hydroxyapatite Bio-gel HTP (BioRad Laboratories, Richmond, Calif.) column. Fractions containing relaxation activity were pooled, diluted and then loaded onto a BioRex70 column (BioRad Laboratories, Richmond, Calif.). The column was developed with a linear gradient from 0.2 to 1M KCl. The peak fractions were pooled and dialyzed overnight at 4° C. against 30 mM potassium phosphate, 50% glycerol (v/v), 0.5 mM EDTA, and 1 mM DTT. Recombinant human topoisomerase I was purified from *Escherichia coli* BL21 (DE3) harboring PET1B as described previously (Gatto et al., Cancer Res., 56, 2795 (1996)).

EXAMPLE 10

Covalent Transfer of $^{32}P$ Radioactivity from DNA to Topoisomerase 1

This phosphate-transfer method was a modification of the procedure described previously by T. C. Rowe et al., J. Biol. Chem., 259, 9177 (1984). Briefly, a 100-$\mu$l reaction mixture containing 10 mM Tris-HCl, pH 7.5, 1 mM $MgCl_2$, 0.5 mM dithiothreitol, 30 $\mu$g/ml of bovine serum albumin, drug (camptothecin or Hoechst 33342) at an indicated concentration, 50 ng of YEpG DNA labeled with $^{32}PdATP$ by the random primer method (Random Primed Labeling Kit, Boehringer Mannheim), and 300 units of human or Aspergillus topoisomerase I, was incubated at 37° C. for 10 minutes. The reactions were terminated by adding NaOH to 0.18M and EDTA to 2.5 mM. After neutralizing the reaction with a precalibrated amount of Tris-HCl, 9 $\mu$l of 0.1M $CaCl_2$ and 7.5 $\mu$l of 20% SDS were added, and the volume was adjusted to 300 $\mu$l with $H_2O$.

Five units of Bal31 nuclease (New England, BioLabs) were added, and the sample was digested for 1 hour at 25° C. The reaction was terminated by extraction with 1 volume of phenol. The phenol phase was saved and back-extracted once with an equal volume of 10 mM Tris-HCl, pH 8.0, 1 mM EDTA. The protein-oligonucleotide complexes were then precipitated from the phenol phase by adding 10 volumes of ice-cold acetone and placing on ice for 10 minutes. The pellet was dissolved in SDS sample buffer and analyzed by SDS-PAGE. Gel drying and autoradiography were done as described (Hsiang et al., J. Biol. Chem., 260, 14873 (1985)).

EXAMPLE 11

Topoisomerase I Relaxation Assay

The relaxation assay was carried out as described by L. F. Liu et al., PNAS USA, 78, 3487 (1981). Briefly, each reaction mixture (20 $\mu$l) contained a mixture of relaxed and supercoiled YEpG DNA (150 ng each) and 1 $\mu$l of Aspergillus or human topoisomerase I diluted to various extents. Following an incubation at 23° or 37° C. for 15 minutes, the reactions were terminated by the addition of 5 $\mu$l of a pre-warmed stop solution (5% sarkosyl, 25% sucrose, 50 mM EDTA, and 0.05 mg/ml bromphenol blue). DNA samples were then analyzed by using a 1% agarose gel in TPE (90 mM Tris-phosphate, 2 mM EDTA, pH 8.0) electrophoresis solution.

EXAMPLE 12

Topoisomerase I Cleavage Assay

DNA topoisomerase I cleavage assays were performed as described by Y.-H. Hsiang et al., J. Biol. Chem., 260, 14873 (1985). YEpG DNA was linearized with BamHI and then 3'-end-labeled with Klenow polymerase and $\alpha[-^{32}P]dCTP$. Following phenol extraction and ethanol precipitation, the labeled DNA was resuspended in 10 mM Tris, pH 8.0, and 1 mM EDTA. The DNA cleavage assay was done in a reaction mixture (20 $\mu$l) containing 40 mM Tris-HCl, pH 7.8, 100 mM KCl, 10 mM $MgCl_2$, 0.5 mM dithiothreitol, 0.5 mM EDTA, 30 $\mu$g/ml bovine serum albumin, 20 ng of labeled YEpG DNA, and 1 ml of Aspergillus or human topoisomerase I diluted to various extents. Following incubation at 23° C. for 15 minutes, the reactions were terminated by the addition of SDS (final concentration 1%) and proteinase K (final concentration 200 $\mu$g/ml). Proteinase K

EXAMPLE 13

Yeast Cytotoxicity Assay

The topoisomerase I-specific in vivo cytotoxicity assay was adapted from A. M. Knab et al., *J. Biol. Chem.*, 268, 22322 (1993). In this system, various topoisomerase I genes or cDNAs cloned into the single-copy yeast plasmid vector (YCpGAL1; Knab et al., cited above) are expressed under the control of the GAL1 promoter in the JN2-134 strain of *S. cerevisiae* (MAT, rad52::Leu2, trp1, ade2-1, his7, ura3-52, ise1, top1-1, and leu2; M. A. Bjornsti et al., *Cancer Res.*, 49, 6318 (1989)). The topoisomerase I gene or cDNA constructs in the vector are, respectively, the wild-type yeast topoisomerase I gene (YCpGAL-ScTOP1; *need cite* (1989)), a nonfunctional topoisomerase I gene where the active site tyrosine-727 is mutated to phenylalanine (YCPGAL1-Sctop1Y727; A. M. Knab et al., *J. Biol. Chem.*, 268, 22322 (1993)), and the wild-type human topoisomerase I cDNA (YCp-GAL-hTOP1; M. A. Bjornsti et al., *Cancer Res.*, 49, 6318 (1989)).

To qualitatively test the cytotoxicity and the topoisomerase I specificity of the drugs, yeast cells containing the specified plasmid were grown in dropout medium supplemented with uracil, 2% galactose, and the drug being tested. It has been established that yeast can survive when topoisomerase I function is obliterated, and that topo I poisons only kill cells having a functional topoisomerase I. Thus, comparison of the relative extent of growth of each of the test strains in the presence of various drugs with that in control plates (no drug) shows: (a) whether the drug has any cytotoxic effects on yeast; (b) whether the cytotoxicity is topoisomerase I-specific; and (c) whether there is any differential specificity of the drugs for yeast compared with human topoisomerase I.

EXAMPLE 14

Characterization of Topoisomerase I from *Aspergillus nidulans*

The plasmid relaxation activity was used to monitor Aspergillus topoisomerase I during purification. The relaxation activity in Aspergillus cell extract was purified through a procedure designed for purification of recombinant human DNA topoisomerase I from *E. coli* (B. Gatto et al., *Cancer Res.*, 56, 2795 (1996)). Several pieces of evidence suggest that the partially purified Aspergillus enzyme is the major nuclear topoisomerase I identified and characterized in other eukaryotic organisms including yeast. First, the purified enzyme is highly active and represents the major DNA relaxation activity in Aspergillus cell extract. From two liters of culture, 30,000 units of topoisomerase I relaxation activity was obtained. Like human topoisomerase I, the Aspergillus enzyme relaxes plasmid DNA to completion and requires neither Mg (II) nor an energy co-factor. Second, the purified Aspergillus enzyme relaxed both negatively and positively supercoiled DNA, a property shared by all eukaryotic nuclear DNA topoisomerase I. Third, the Aspergillus enzyme is sensitive to inhibition by camptothecin and Hoechst 33342 (Ho33342) which are known to inhibit (poison) human nuclear topoisomerase I.

The sensitivity of the Aspergillus enzyme to camptothecin and Hoechst 33342 was initially indicated by a phosphate-transfer experiment which was designed to determine the approximate reduced molecular weight of the enzyme. In this experiment, $^{32}$P-labeled DNA was reacted with Aspergillus topoisomerase I to form covalent protein-DNA complexes. The covalent complex of topoisomerase I-DNA was digested with Bal31 to reduce the size of the labeled-oligonucleotide which is covalently linked to topoisomerase I.

Using this phosphate-transfer method, Aspergillus topoisomerase I was identified as a 105 kDa protein which is slightly larger than recombinant human topoisomerase I (100 kDa). The lower band at approximately 75 kDa position is known to be a proteolytic degradation product of 100 kDa human topoisomerase I. The effect of the residual oligonucleotide on the mobility of topoisomerase I is apparently negligible. Interestingly, both camptothecin (100 mM) and Ho33342 (1 mM) stimulated the phosphate transfer as evidenced by the enhanced labeling of 105 kDa Aspergillus topoisomerase I.

At higher concentrations of Ho33342, the phosphate transfer was progressively inhibited. This effect of camptothecin and Ho33342 is discussed below.

EXAMPLE 15

Camptothecin and Ho33342 Are Potent Inhibitors of Aspergillus Topoisomerase I The phosphate-transfer experiment suggested that both camptothecin and Ho33342 may inhibit Aspergillus topoisomerase I by a poisoning mechanism. In order to test this possibility, Aspergillus topoisomerase I was used in a DNA cleavage reaction in the presence of various drugs. Both camptothecin (CPT) and Ho33342 (HOE) are potent inhibitors of Aspergillus topoisomerase I. Extensive DNA cleavage was observed at concentrations as low as 1.0 and 0.1 mg/ml for camptothecin and Ho33342, respectively.

Interestingly, nitidine and coralyne, which are known to be highly potent inhibitors of human DNA topoisomerase I, did not inhibit Aspergillus topoisomerase I to any significant extent. DM/II/33, another highly potent inhibitor of human DNA topoisomerase I, was only weakly inhibitory toward Aspergillus topoisomerase I. Berenil, which is inactive against human topoisomerase I, was also inactive against Aspergillus topoisomerase I.

These results indicate that human and Aspergillus topoisomerase I are substantially different in terms of their sensitivity toward various enzyme inhibitors. It is also interesting to note that at the highest concentration of Ho33342 (10 mg/ml), topoisomerase I-mediated DNA cleavage was dramatically inhibited. This cleavage-inhibitor effect at higher concentrations of inhibitors has been described previously for a number of intercalators and DNA minor groove binding ligands (A. Y. Chen et al., *PNAS USA*, 90, 8131 (1993)) and attributed to inhibition of enzyme binding to the DNA template (K. M. Tewey et al., *Science*, 226, 466 (1985)). The inhibitory effect of Ho33342 on phosphate-transfer to Aspergillus topoisomerase I can therefore be similarly explained.

EXAMPLE 16

Selective Sensitivity of Aspergillus Topoisomerase I to Bi- and Ter-benzimidazoles Previous studies have identified a number of mono-, bi- and ter-benzimidazoles as effective inhibitors (poisons) of mammalian DNA topoisomerase I. To test whether Aspergillus topoisomerase I is also sensitive to the inhibitory effect of these benzimidazoles, a number of compounds were screened using the cleavage assay. Aspergillus topoisomerase I (60 units/reaction) was strongly inhibited (poisoned) by 13 and 11, both of which are terbenzimidazoles. None of the mono-benzimidazoles, including QS/II/50, QS/II/51, QS/II/59A, an QS/II/9, exhibited any inhibitory effect on Aspergillus topoisomerase I. Previous studies have established that all these mono-benzimidazoles except QS/II/50 are inhibitors (poisons) of mammalian DNA topoisomerase I. The selective sensitivity of Aspergillus topoisomerase I to bi- (e.g., Ho33342 and compound 2 wherein n is 3) and ter- (e.g., 13 and 11), but not mono-benzimidazoles (e.g., QS/II/9) again indicates differences in drug sensitivity between the human and Aspergillus enzymes.

EXAMPLE 17

Differences in Cleavage Specificity between Human and Aspergillus Topoisomerase I In addition to differences in drug sensitivity between human and Aspergillus topoisomerase I, additional differences in cleavage specificity have been observed between humans and Aspergillus topoisomerase I. The cleavage patterns of human (labeled hTOP1, 150 units/reaction) and Aspergillus (labeled AnTOP1, 60 units/reaction) enzymes are dramatically different in the presence of the bibenzimidazole Ho33342 (HOE). The larger number of cleavage sites and the larger extent of cleavage exhibited by Aspergillus topoisomerase I in the presence of HOE are not understood. Although less obvious, the cleavage patterns of the human and Aspergillus enzymes were also different in the presence of camptothecin (CPT).

To rule out the possibility that contaminating topoisomerase II in Aspergillus topoisomerase I enzyme preparation may contribute to the cleavage pattern, part of the samples were also analyzed for possible double-stranded breaks. No double-stranded DNA breaks were observed when DNA samples were analyzed by neutral rather than alkaline loading. It is also evident from this experiment that Aspergillus topoisomerase I is less sensitive to CPT than the human enzyme.

The differences in cleavage specificity between human (150 units/reaction) and Aspergillus (60 units/reaction) enzymes were also evident when terbenzimidazoles (13 and 11) were used at 0.1, 1.0 and 10 μg/ml. In addition, the Aspergillus enzyme appeared to be substantially more sensitive to 13 than the human enzyme.

EXAMPLE 18

Yeast and Aspergillus Topoisomerase I Enzymes Exhibit Similar Drug Sensitivity/Resistance Yeast top1 deletion strains expressing human or yeast topoisomerase I under identical conditions have been used to evaluate differential drug sensitivity of the human and yeast enzymes (J. Nitiss et al., *PNAS USA,* 85, 7501 (1988); B. Gatto et al., *Cancer Res.,* 56, 2795 (1996)). Although yeast cells expressing yeast topoisomerase I are camptothecin-sensitive, they are at least ten times more resistant to camptothecin than yeast cells expressing human topoisomerase I. Nitidine, DM/II/33, and QS/II/9 are highly cytotoxic against yeast cells expressing human topoisomerase I, but not cytotoxic to yeast cells expressing either functional or nonfunctional yeast topoisomerase I. These results indicate that yeast and Aspergillus topoisomerase I are resistant to the same drugs (i.e., nitidine, the protoberberine DM-II-33 and the mono-benzimidazole QS-II-9) that poison human topoisomerase I.

Thus, Aspergillus topoisomerase I, like human topoisomerase I, is sensitive to the poisoning activity of camptothecin, the bibenzimidazole Ho33342 and terbenzimidazoles (11 and 13). Although camptothecin appears to be less active against the Aspergillus than the human enzyme, the terbenzimidazole 11 appears to be more active against the Aspergillus than the human enzyme. The effectiveness of the terbenzimidazoles against Aspergillus topoisomerase I is not restricted to 11 and 13, the terbenzimidazoles of formula I wherein n=1, X=H, Ar=5-phenyl, Y=H and Y' is ethyl or 4-methoxyphenyl, and the 4-phenyl-isomer of compound 13, are also effective against the fungal enzyme in vitro. The general higher sensitivity of Aspergillus topoisomerase I to terbenzimidazoles is not understood. However, as judged from the higher extent of cleavage and looser sequence specificity of cleavage, one may argue that Aspergillus topoisomerase I may be less sensitive to the inhibitory effect of these DNA binding ligands. In other words, Aspergillus topoisomerase I may bind DNA with higher affinity than the human enzyme and therefore is less susceptible to the inhibitory effect of these DNA binding ligands.

All publications and patents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method to treat fungal infection comprising administering to a mammal afflicted with a fungal infection, an effective antifungal amount of a compound of the formula:

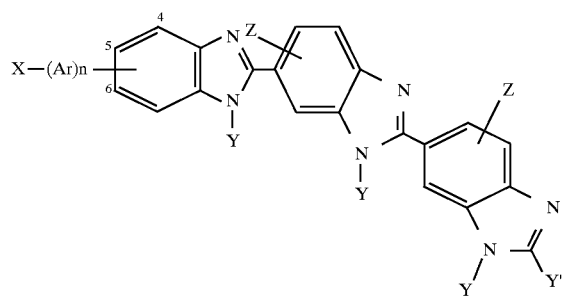

wherein Ar is $(C_6-C_{12})$aryl, (5- to 12-membered)heteroaryl comprising 1–3 N, S or non-peroxide O, wherein N is unsubstituted or is substituted with H, $(C_1-C_4)$alkyl or benzyl; X is H, CN, CHO, OH, acetyl, $CF_3$, $O(C_1-C_4)$alkyl, $NO_2$, $NH_2$, halogen or halo-$(C_1-C_4)$alkyl; each of Y is H, $(C_1-C_4)$alkyl or aralkyl; Y' is H, $(C_1-C_4)$alkyl, phenyl or methoxyphenyl; each Z is individually H, $(C_1-C_4)$alkyl, halogen or halo$(C_1-C_4)$alkyl; and n is 0–1; or a pharmaceutically acceptable salt thereof.

2. The method of claim 1 wherein n is 1 and Ar is at the 5-position.
3. The method of claims 1 or 2 wherein Ar is phenyl.
4. The method of claims 1 or 2 wherein Ar is 2-pyridyl.
5. The method of claim 3 wherein X is halogen.
6. The method of claim 5 wherein X is Cl.

7. The method of claim 6 wherein X—Ar is p-chlorophenyl.

8. The method of claim 7 wherein Y' is H; each Y is H; and each Z is H.

9. The method of claim 1 wherein n is 0.

10. The method of claim 9 wherein X is Cl.

11. The method of claim 9 wherein X is Br.

12. The method of claims 10 or 11 wherein Y' is H, $CH_3$, ethyl or 4-methoxyphenyl; each Y is H; and each Z is H.

13. The method of claim 1 wherein Z is H, F, $CH_3$ or $CF_3$.

14. The method of claim 1 wherein Ar is benzo.

15. The method of claim 13 wherein Ar is 4,5-benzo.

16. The method of claim 13 wherein Ar is 5,6-benzo.

17. The method of claim 1 wherein said compound is systemically administered.

18. The method of claim 17 wherein said compound is orally administered.

19. The method of claim 1 wherein said compound is parenterally administered.

20. The method of claim 19 wherein said compound is topically administered.

21. The method of claim 19 wherein said compound is administered intravenously.

22. The method of claim 1 wherein the mammal is a human.

23. The method of claim 1 wherein the fungal infection is a systemic infection.

24. The method of claim 1 wherein the compound is administered in combination with a pharmaceutically acceptable vehicle.

* * * * *